Jan. 19, 1937. B. A. BOURNE Plant Pat. 220
SUGARCANE
Filed Oct. 1, 1936
FIG. I
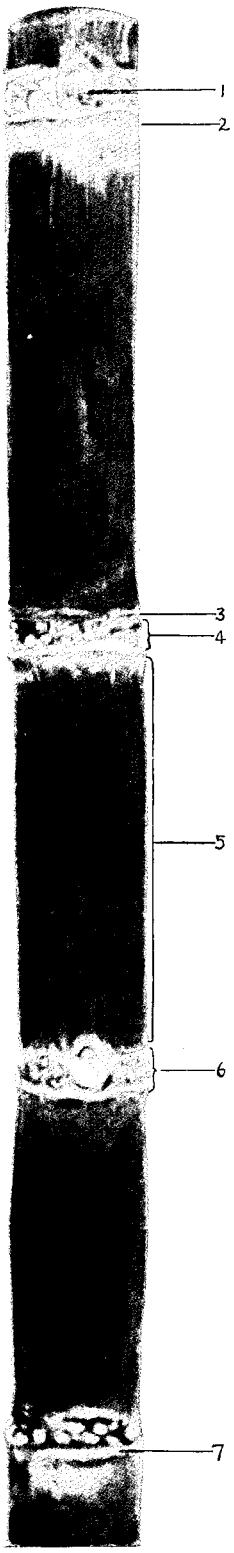
FIG. II
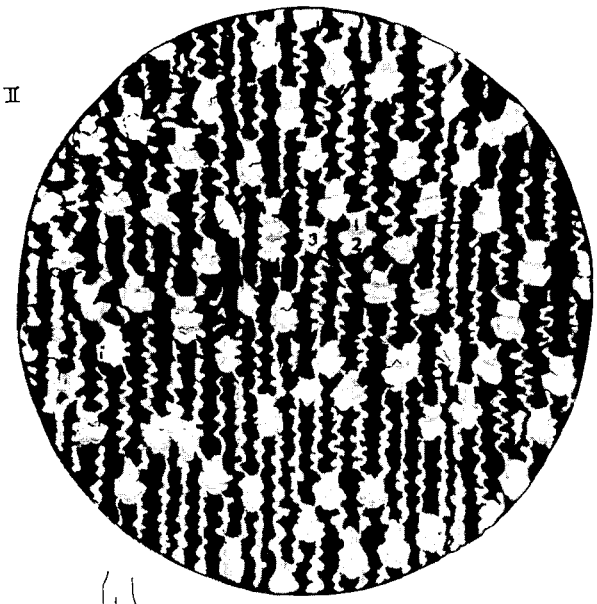
FIG. III
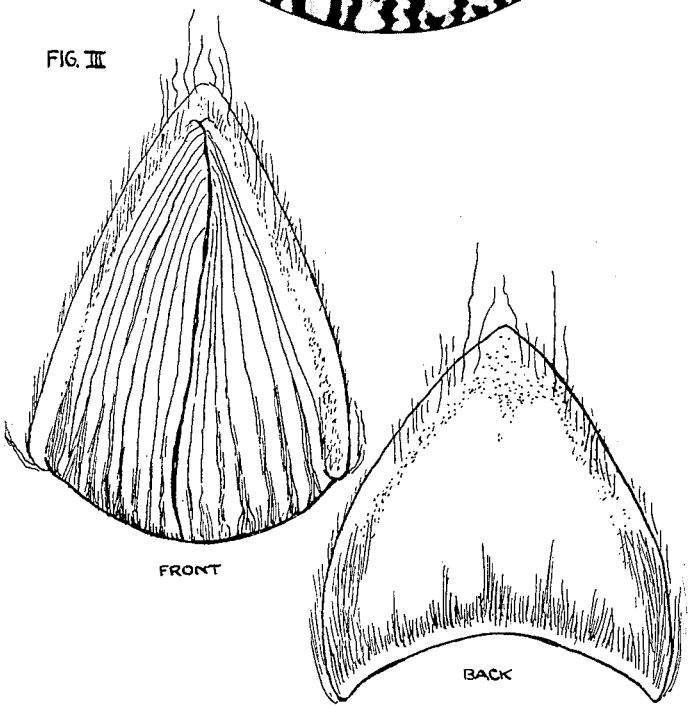
INVENTOR
Benjamin Arthur Bourne
By Orville M. Kile
PLANT PATENT AGENT Patented Jan. 19, 1937

Plant Pat. 220

UNITED STATES PATENT OFFICE

220

SUGAR CANE

Benjamin Arthur Bourne, Clewiston, Fla.

Application October 1, 1936, Serial No. 103,601

1 Claim. (Cl. 47—59)

My new variety originated as a seedling and is the result of definite breeding efforts carried on by me in December, 1931. It was secured by crossing the mother cane P. O. J. 2725 with the male parent C. P. 27–35.

This variety has stalks very large in diameter and solid in cross-section. It is moderately early in rate of maturity in the fall. As a germinator it is excellent, producing a large number of primary shoots early in growth, thus cutting down re-planting and cultivation costs. It does not have the objectionable character of producing "suckers" late in the season which would result in immature stalks at harvest time. Because of the excellent stalk diameter, solidity and weight, it can be harvested readily at the cheapest rate per ton.

When planted in the Everglades of Florida during the fall or early winter, it will by the end of the following November give satisfactory yields of cane sugar (sucrose) amounting to from 7 to 8 percent by weight of the cane. If not harvested in the fall (or about a year from date of planting, if same was done in the fall) it will gradually increase in sugar (sucrose) content for from 4 to 5 months, reaching a maximum of 9 to 14 percent cane sugar (by weight of the cane), depending on soil type, weather conditions and suitable fertilization. If frozen after reaching a stage of maturity suitable for harvesting (8% cane sugar by weight), the rate of deterioration of sucrose in the stalks is decidedly slow, enabling milling operations to proceed for a long period without difficulty.

As a result of studies conducted over a period of 5 years in Florida, this variety has been found to be very resistant to leaf diseases due to *Helminthosporium*, very resistant to red rot of the stalk (due to *Colletotrichum falcatum*) and immune to present strains of mosaic disease. It has also proved to be very resistant to wind damage, its strong root system preventing uprooting of stools under severe weather conditions.

When harvested from early November onwards, it exhibits excellent ratooning power, in spite of being frosted back several times during the winter. Ratoon growth is so strong in the spring that the rows soon close in, thus cutting down cultivation costs.

In tonnage production of millable cane, it has proved in comparative tests in the Florida Everglades to rank very high, especially if harvested during the mid-winter period. Yields of 49 to 64 tons per acre as plant cane have been secured, the highest returns being from muck lands in frost-free location and with good mineral content.

The original illustration shows: Fig. I—mid-sections of typical stalks showing the color variations, Fig. II—typical structure of stem epidermis magnified 295 times and Fig. III—the front and back views of a typical stem bud.

The following is a detailed description of my new variety of sugar cane.

*The stalk*

*Structure.*—Stalks are very solid in cross-section and firm. When compared with other sugar canes, they are low in fiber content.

*Growth.*—Stalks are semi-erect from the start and either remain thus, or are recumbent later in the growth cycle. They may attain a length of from 7 to 10 feet or more, depending on soil type, weather conditions, fertilization and period of growth.

*Size.*—Diameter of stalk as measured from the middles of 20 stalks selected at random (on good "Okeechobee" soil type), varied from 2.5 centimeters to 3.7 centimeters, averaging 3.25 centimeters.

*Internodes*—Fig. I—5.—In middle of stalk frequently reach a length of 15 centimeters, but varied from 12 centimeters to 16 centimeters, averaging from ten random measurements 14.3 centimeters. They follow one another almost in a straight line, but are frequently definitely "staggered".

*Nodes.*—Somewhat constricted, especially in the vicinity of the wax rings toward the top of the stalk, when compared with the middle of the internodal portion. (Fig. I—6.)

*Color.*—Greenish-brown or green at base, but becoming reddish-purple-brown or red and green toward middle and top. Typical colors and markings on middle stalk portions are shown in Fig. I.

*Furrows* (or eye grooves immediately above the eyes.)—Usually absent, but a very slight one has been noted to occur rarely. (Fig. I—above 1).

*Wax or "bloom".*—Only a very slight bloom present on surface of stem. The "wax ring" is usually plainly present below the node. (Fig. I—2.)

*Root band.*—Color is purplish red and green; shape is oblique. Width varies from 0.3 to 0.7 centimeter. (Fig. I—4).

*Growth ring.*—Color is yellow-green at first and later reddish-brown. Shape is slightly elevated. (Fig. I—3).

*Rind.*—Splitting or cracking of the rind almost never occurs and when it does, no damaging effects result.

*Leaf scar.*—Prominent. (Fig. I—7.)

*Leaves*

*Blade.*—Medium green in color; width 6.5 to 7.5 centimeters across widest portion of mature outer blades. Grows somewhat semi-erect and with top overhanging.

*Leaf sheath.*—Young ones usually with sharp hairs present, but old sheaths become smooth or glabrous.

*Throat.*—Coated with wool-like felted hairs.

*Collar.*—The triangular areas do not meet or coalesce at the midrib. Surface waxy.

*Ligule.*—Length 0.4 centimeter. Edge fimbriate.

*Leaf stripping.*—The dead leaves and leaf sheaths usually fall away from the stalk at maturity very readily, thus assisting rapid harvesting operations without burning.

*Stem buds*

*Size.*—Good, ranging from 1.0 to 1.3 centimeters wide by 1.1 to 1.7 centimeters long.

*Position.*—Not prominent, that is, they do not protrude much from the surface of the stalk. Thus in handling the cane for planting purposes, little bud damage occurs. The tip of the bud protrudes above the growth ring (Fig. I—1) and the base is usually situated near the base of the leaf sheath.

*Form.*—For typical form and hair groups, see Fig. III, showing both front and back views.

*Stem epidermal cells*

The average width of epidermal cells is approximately 14.6 microns, which places the variety in a group of canes having what is considered wide epidermal cells. The number of short-cell groups (Fig. II, 1 and 2) per square millimeter is approximately 690. The number of stomata per microscopic circular field of 1.9 square millimeters averaged from ten observations 1.3, varying usually from 1–2. Pointed, elongated cork cells are occasionally present. Solitary cork cells are abundant (Fig. II—3). No solitary silica cells (Fig. II—1) have ever been observed to occur.

*Inflorescence*

This variety frequently blooms fairly abundantly late in the season (March) on muck lands protected from frost and of high mineral content in the Florida Everglades. Inflorescences are large and well formed. No fertile pollen has yet been observed, but the ovaries appear to be normal and have purple, fully developed stigmas.

The principal characteristics which in combination help to distinguish my new variety from all other known varieties of sugar cane are:

1. Moderately early in maturity.
2. Different color and shape of (*a*) stalk and (*b*) bud.
3. Different pattern of stem epidermis.
4. Semi-erect growth habit of leaves and stalks, the latter becoming recumbent toward maturity. Leaves medium green in color.
5. High tonnage and sugar producing ability per acre on the better as well as some of the poorer types of Everglades soils.
6. Marked resistance to certain fungus leaf diseases common to sugar cane and also immunity to certain existing strains of mosaic virus.
7. Strength of root system.
8. Absence of damage due to splitting of rind.
9. Very large size and solidity of stalk.
10. Good sized buds, located in a protected position.
11. Prolific, early stooler without producing late "suckers".
12. Production of large, well formed inflorescences on certain soils in the Everglades of Florida only late in the flowering season.

Having thus disclosed my invention, what I claim as new is:

The variety of sugar cane herein shown and described, characterized particularly by its resistance and immunity to certain diseases, high tonnage of cane, moderate earliness, distinctive color and shape of stalk and bud, distinctive pattern of stem epidermis, very large diameter and solid, heavy stalks.

BENJAMIN ARTHUR BOURNE.